(12) United States Patent
Anderson

(10) Patent No.: US 8,915,868 B1
(45) Date of Patent: Dec. 23, 2014

(54) INSTRUMENT FOR MEASURING THE POSTURE OF A PATENT

(76) Inventor: Kendall Duane Anderson, Charles, SD (US)

( * ) Notice: Subject to any disclaimer, the term of this patent is extended or adjusted under 35 U.S.C. 154(b) by 267 days.

(21) Appl. No.: 13/558,040

(22) Filed: Jul. 25, 2012

Related U.S. Application Data

(60) Provisional application No. 61/522,398, filed on Aug. 11, 2011.

(51) Int. Cl.
- *A61B 5/117* (2006.01)
- *A61B 5/103* (2006.01)
- *A61B 1/00* (2006.01)
- *G01B 1/00* (2006.01)

(52) U.S. Cl.
USPC ................................ 600/594; 33/511; 33/512

(58) Field of Classification Search
USPC .............................. 600/587, 594; 33/511, 512
See application file for complete search history.

(56) References Cited

U.S. PATENT DOCUMENTS

| | | | |
|---|---|---|---|
| 889,224 A | 6/1908 | Haas | |
| 1,271,461 A | 7/1918 | Hanna | |
| 1,735,854 A | 11/1929 | Emerson | |
| 1,846,528 A | 2/1932 | Santin | |
| 2,111,648 A | 3/1938 | Stone | |
| 2,295,447 A | 9/1942 | Bierman | |
| 2,324,672 A | 7/1943 | Bierman et al. | |
| 2,374,105 A | 4/1945 | Kraus | |
| 3,256,611 A | 6/1966 | Deming | |
| 4,135,498 A | 1/1979 | McGee | |
| 4,425,713 A | 1/1984 | Rotella | |
| 4,699,156 A | 10/1987 | Gracovetsky | |
| 4,708,148 A | 11/1987 | Olson | |
| 4,971,069 A | 11/1990 | Gracovetsky | |
| 5,038,489 A | 8/1991 | Muehlenbein | |
| 5,080,109 A | 1/1992 | Arme, Jr. | |
| 5,471,995 A | 12/1995 | Halliday | |
| 6,007,459 A | 12/1999 | Burgess | |
| 6,231,527 B1 | 5/2001 | Sol | |
| 6,237,239 B1 | 5/2001 | Miyazaki | |
| 6,387,061 B1 | 5/2002 | Nitto | |
| 6,415,199 B1 | 7/2002 | Liebermann | |
| 6,468,233 B2 | 10/2002 | Cook | |
| 6,514,219 B1 | 2/2003 | Guimond et al. | |
| 6,524,260 B2 | 2/2003 | Shechtman et al. | |
| 6,565,519 B2 | 5/2003 | Benesh | |
| 6,602,210 B2 | 8/2003 | Savet | |
| 7,029,031 B2 | 4/2006 | Moisel et al. | |
| 7,131,952 B1 | 11/2006 | Dickholtz, Sr. et al. | |
| 7,291,118 B2 | 11/2007 | McFarland et al. | |
| 7,335,167 B1 | 2/2008 | Mummy | |
| 7,353,151 B2 | 4/2008 | Furusu et al. | |
| 7,387,611 B2 | 6/2008 | Inoue et al. | |
| 7,616,779 B2 | 11/2009 | Liao et al. | |
| 7,633,527 B2 | 12/2009 | Pilu | |
| 7,715,605 B2 | 5/2010 | Verre et al. | |

(Continued)

*Primary Examiner* — Brian Szmal
(74) *Attorney, Agent, or Firm* — Plager Schack, LLP

(57) ABSTRACT

The disclosed invention is an instrument for measuring posture in a patient. The instrument comprises a measuring instrument, further comprising a perpendicular member mechanically coupled to a fixed marker and a sliding marker. The fixed marker and the sliding marker can mark a poster instrument. The poster instrument is mechanically coupled to right side banner track which is mechanically coupled to three track screws, a left side banner track which is mechanically coupled three track screws and an upper banner track, which is mechanically coupled to an upper track screw. An examiner can utilize the measuring instrument to mark the poster instrument and maneuver the track screws to determine difference in measurements at head, shoulders, iliac crests, and vertical head measurement in a repeatable and consistent manner.

4 Claims, 3 Drawing Sheets

(56) References Cited

U.S. PATENT DOCUMENTS

| | | |
|---|---|---|
| 7,770,301 B1 | 8/2010 | Grandberry et al. |
| 7,891,106 B2 | 2/2011 | Dunham |
| 7,914,473 B2 | 3/2011 | Josey |
| 2004/0111909 A1 | 6/2004 | Pourmanafzadeh |
| 2005/0027216 A1 | 2/2005 | Guillemaud et al. |
| 2007/0083384 A1 | 4/2007 | Geslak et al. |
| 2009/0030350 A1 | 1/2009 | Yang et al. |
| 2010/0010432 A1 | 1/2010 | Skelton |
| 2010/0069795 A1 | 3/2010 | Kang et al. |
| 2010/0113961 A1 | 5/2010 | Ohlander et al. |
| 2010/0278391 A1 | 11/2010 | Hsu et al. |
| 2011/0025834 A1 | 2/2011 | Chen et al. |
| 2011/0054358 A1 | 3/2011 | Kim et al. |
| 2011/0172567 A1 | 7/2011 | Panken et al. |

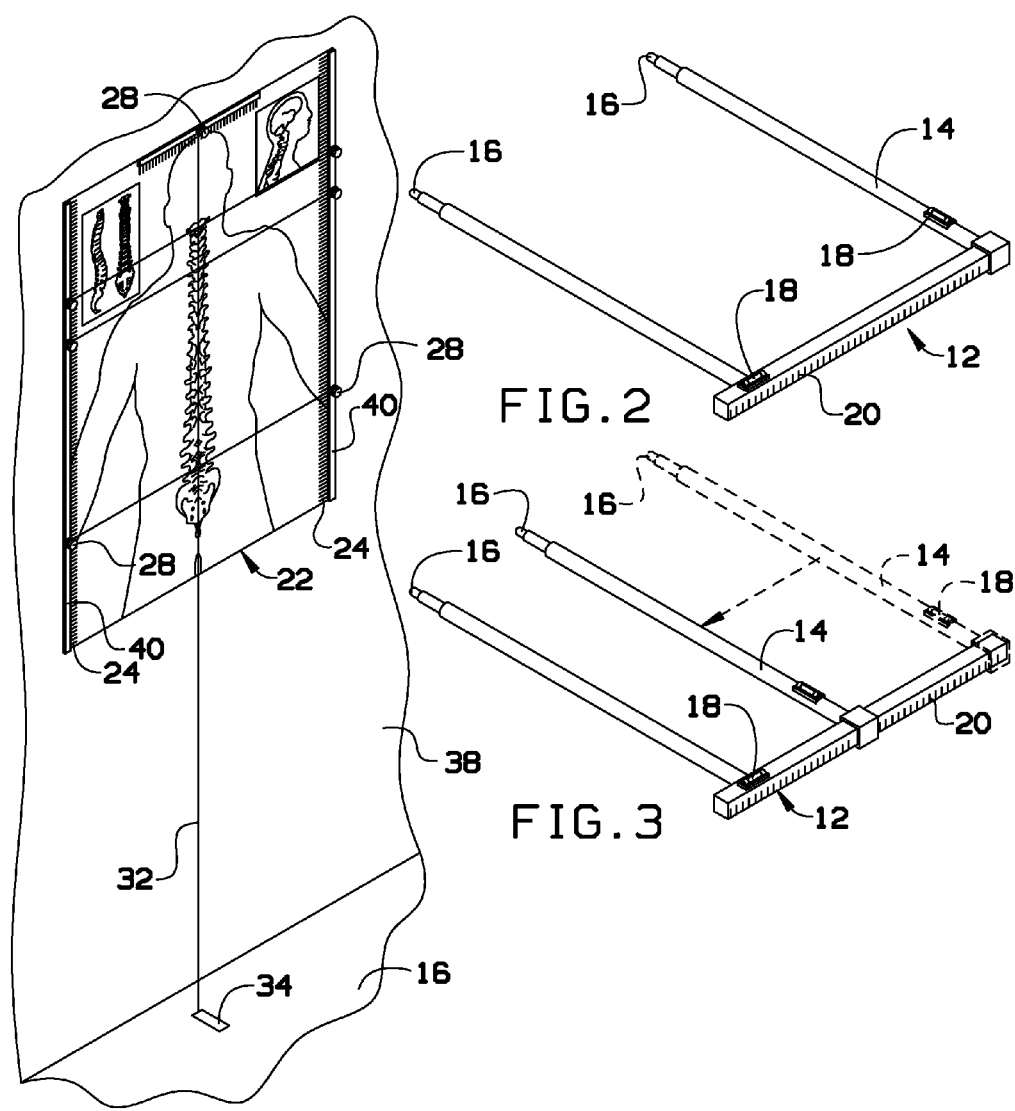
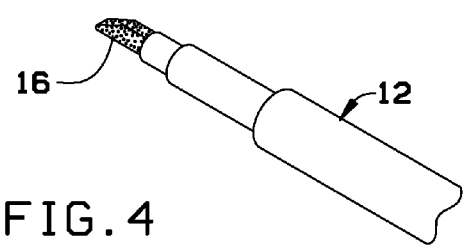

INSTRUMENT FOR MEASURING THE POSTURE OF A PATENT

CROSS REFERENCE TO RELATED APPLICATIONS

This application claims priority to U.S. Provisional Patent Application No. 61/522,398 filed on Aug. 11, 2011.

FIELD OF THE INVENTION

This invention relates to equipment to diagnose and track a medical condition or state of being in a patient.

BACKGROUND OF THE INVENTION

Historically, diagnosis of posture has been done by taking multiple x-rays and analyzing them. More recently, Posture-Pro has used a digital camera to take digital photographs and then analyze the photographs by drawing points and collecting the points with lines (see www.posturepro.com). Much like the use of x-rays, Posture Pro is not accurate as it is very subjective, where the examiner places the dots on the digital pictures for line drawings. In recent years, equipment that diagnoses posture has come onto the market. However, this equipment, shown in U.S. Pat. No. 7,131,952 issued to Dickholtz still has many of the difficulties of the prior art, most notably the relative difficulty of calibrating a large machine attached to the patient and subjective analysis in reading the accompanying results. Even if results could be obtained reliably, Dickholtz fails to take a vertical head reading, rendering the results incomplete or the patient being sent back to the x-ray room for further analysis.

The present invention solves these problems.

BRIEF SUMMARY OF THE INVENTION

The disclosed invention is an instrument for measuring posture in a patient. The instrument comprises a measuring instrument, further comprising a perpendicular member mechanically coupled to a fixed marker and a sliding marker. The fixed marker and the sliding marker can mark a poster instrument. The poster instrument is mechanically coupled to right side banner track which is mechanically coupled to three track screws, a left side banner track which is mechanically coupled three track screws and an upper banner track, which is mechanically coupled to an upper track screw. An examiner can utilize the measuring instrument to mark the poster instrument and maneuver the track screws to determine difference in measurements at head, shoulders, iliac crests, and vertical head measurement in a repeatable and consistent manner.

BRIEF DESCRIPTION OF THE SEVERAL VIEWS OF THE DRAWINGS

Having thus described the invention in general terms, reference will now be made to the accompanying drawings, which are not necessarily drawn to scale, and wherein:

FIG. 1 is a perspective view of the invention.

FIG. 2 is a perspective view of the measuring instrument only.

FIG. 3 is a perspective view of the measuring instrument only and illustrating exemplary sliding range of motion of the measuring instrument slide device.

FIG. 4 is a detail perspective view of the measuring instrument only.

Figure 5:
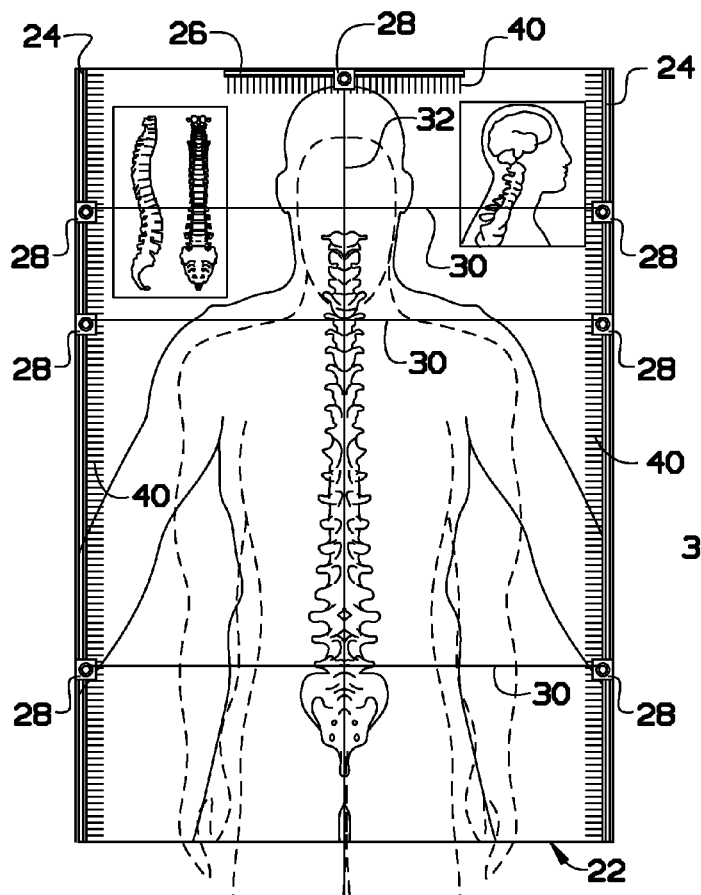

FIG. 5 is a front view of the invention shown in use.

Figure 6:
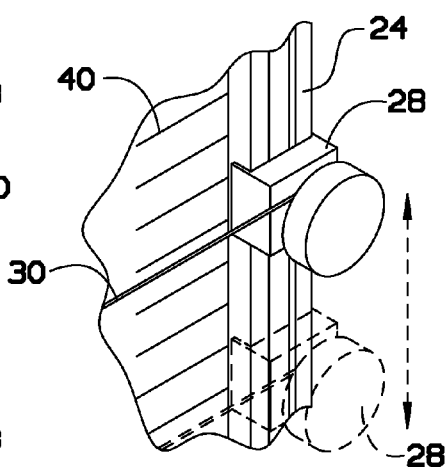

FIG. 6 is a detail perspective view of the invention illustrating sliding action of the banner track screw.

Figure 7:
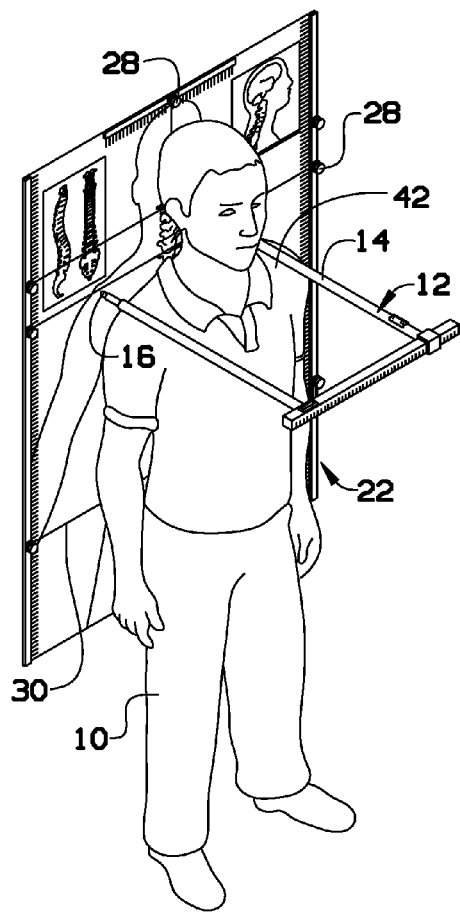

FIG. 7 is a perspective view of the invention shown in use.

Figure 8:
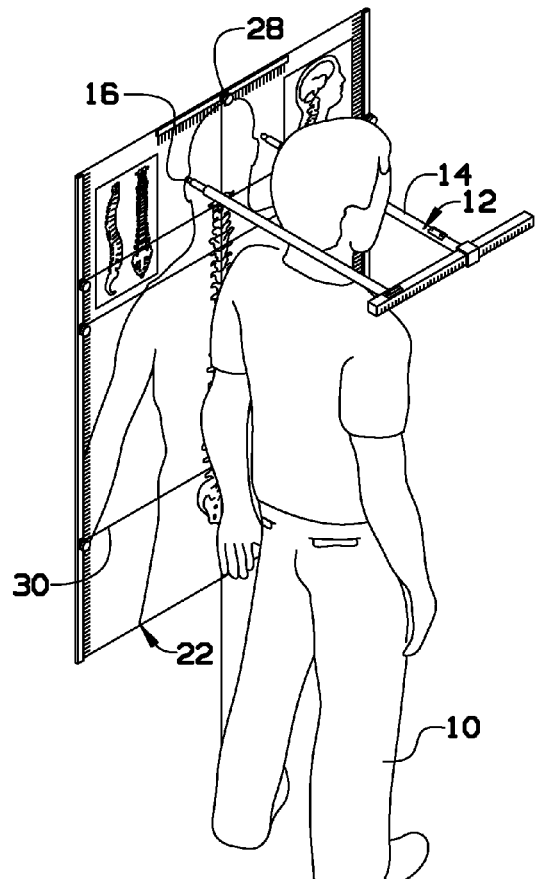

FIG. 8: is a perspective view of the invention shown in use.

DETAILED DESCRIPTION OF THE INVENTION

Embodiments of the present invention overcome many of the obstacles associated with diagnosing the posture of a patient and now will be described more fully hereinafter with reference to the accompanying drawings that show some, but not all embodiments of the claimed inventions. Indeed, the invention may be embodied in many different forms and should not be construed as limited to the embodiments set forth herein. Rather, these embodiments are provided so that this disclosure will satisfy applicable legal requirements. Like numbers refer to like elements throughout.

FIG. 1 and FIG. 5 show perspective views of poster instrument 22, which is mounted onto wall 38. Poster instrument 22 is mechanically coupled to right side banner track 24 which is further mechanically coupled to a right eye-level track screw 28, a right shoulder-level track screw 28 and a right hip-level track screw 28. Poster instrument 22 is further mechanically coupled to left side banner track 24 which is further mechanically coupled to a left eye-level track screw 28, a left shoulder-level track screw 28 and a left hip-level track screw 28. Poster instrument 22 is further mechanically coupled to upper banner track 26 which is mechanically coupled to upper track screw 28. Upper banner track 26, left banner track 24 and right banner track 24 are immediately adjacent to measurement markings 40.

Left eye-level track screw 28 is mechanically coupled to right eye-level track screw 28 by eye-level string 30. Left shoulder-level track screw 28 is mechanically coupled to right shoulder-level track screw 28 by shoulder-level string 30. Left hip-level track screw 28 is mechanically coupled to right hip-level track screw 28 by hip-level string 30. Upper track screw 28 is mechanically coupled to floor tape 34 on floor 16 by vertical string 32. Vertical string 32 covers vertical line which parallels vertical string 32 on poster instrument 22.

FIG. 2, FIG. 3 and FIG. 4 show measuring instrument 12 in detail. Measuring instrument 12 comprises marked perpendicular member 20 mechanically coupled to fixed marker 16 and sliding marker 16. Marked perpendicular member 20 is mechanically coupled to horizontal level 18 and sliding marker 16 is mechanically coupled to vertical level 18. Marker 16 can make a mark on poster instrument 22, in some instances, with a dry erase marker.

FIG. 5, FIG. 6, FIG. 7 and FIG. 8 provide detail on how to use the instrument for measuring the posture of a patient. First, patient 10 stands with one's back just in front of poster instrument 22 without touching poster instrument 22. An examiner can instruct patient 10 to line one's feet on either side of tape 34 with as much of a natural stance as patient 10 can.

Next, colored tape is placed just lateral to the Acromial Clavicular joints and at the middle of the left humoral head. This is in the vicinity of the shoulder-level string 30.

At this point, the examiner may want to place a strap or belt around the waist of the patient at the level of the iliac crest, which is in the vicinity of the hip-level string. The strap or belt can help keep the clothing of patient 10 next to the body of patient 10.

Next, the examiner uses marking instrument 12 to place marks on poster instrument 22 with marker 16 at the level of the eyes of patient 10. This should be in the vicinity of the eye-level string 30. After that, the examiner uses marking instrument 12 to place marks on poster instrument 22 with marker 16 at the level of the colored tape that have been placed at the Acromial Clavicular joints of patient 10. This should be in the vicinity of the shoulder-level string 30. Following that, the examiner uses marking instrument 12 to place marks on poster instrument 22 with marker 16 at the level of the iliac crests of patient 10. This should be in the vicinity of the hip-level string 30. The examiner should use vertical level 18 to level measuring instrument 12 just before making marks on the poster with marker 16.

After that, the examiner should instruct patient 10 to turn with the left shoulder of patient 10, marked with colored tape on center of left humoral head, on the vertical line underneath vertical string 32, again asking patient 10 to take a natural stance. The examiner should place the left fork of measuring instrument 12, touching the occiput, which is back of head at base of skull, at the level of the right ear opening of patient 10. The right fork of the measuring instrument is in front of the face of patient 10. The examiner should use the horizontal level 18 for accuracy and then make a mark at the level of the right ear opening and in front of the face.

The examiner should then measure the distance, with measuring instrument 12, from the back of the occiput to the ear opening, calculating the distance between the level of the occiput and the right ear opening. After this the examiner should subtract 1 cm as the center of fixed marker 16 to the edge of fixed marker 16 is 1 cm.

Next, the examiner places a mark at on poster instrument 22 with the measurement found from the back of the head to the ear opening. The examiner should reduce the distance between fixed marker 16 and sliding marker 16 to that distance. The examiner next measures the distance from the vertical line to the ear opening mark on the poster. This is the forward head posture reading for patient 10. When the mark is to the left of the vertical line, the forward head posture reading for patient 10 would be read as a negative number. When the mark is to the right of the vertical line, the forward head posture reading for patient 10 would be read as a positive number.

Next, the examiner connects the eye level-markings with eye-level horizontal string 30 by maneuvering left eye-level track screw 28 and right eye-level track screw 28 until the eye-level markings connect creating an eye measurement. The examiner connects the shoulder level-markings with shoulder-level horizontal string 30 by maneuvering left shoulder-level track screw 28 and right shoulder-level track screw 28 until the shoulder-level markings connect creating a shoulder measurement. The examiner connects the hip-level markings with hip-level horizontal string 30 by maneuvering left hip-level track screw 28 and right hip-level track screw 28 until the hip-level markings connect creating a iliac crests measurement.

After the measurements are taken, the examiner can evaluate the difference in measurements at the head, shoulders, iliac crests, and the vertical head measurement. An examiner can change the measurements from centimeter increments into degrees by using simple geometry as explained in Dickholz. The examiner can write on poster instrument 22 to show patient 10 the degree of difference as this will help in educating patient 10 as to posture. The summation of the difference in measurements at the head, shoulders, iliac crests, and the vertical head measurement once each of those has been converted into an angle is the first posture number the forward head measurement is the second posture number. This procedure is consistent and can lead to repeatable results regardless of the examiner taking the measurements.

Patient 10 is given a posture number. The posture number is the degrees of difference and the forward head posture. Ex. (8+2).

The examiner can use the posture number on an exam form to show the posture deviations with a posture number and to plot patient 10 posture measurements.

That which is claimed:

1. An instrument for measuring posture in a patient, the instrument comprising,
    a measuring instrument, further comprising a perpendicular member mechanically coupled to a fixed marker and a sliding marker;
    the fixed marker and the sliding marker are configured to mark a poster instrument;
    the poster instrument is mechanically coupled to right side banner track which is further mechanically coupled to aright eye-level track screw, a right shoulder-level track screw and a right hip-level track screw;
    the poster instrument is further mechanically coupled to left side banner track which is further mechanically coupled to a left eye-level track screw, a left shoulder-level track screw, and a left hip-level track screw;
    wherein the right eye-level track screw and the left eye-level track screw are configured to be moved along the left side banner track and the right side banner track to represent an eye level of the patient;
    wherein the right shoulder-level track screw and the left shoulder eye-level track screw are configured to be moved along the left side banner track and the right side banner track to represent a shoulder level of the patient;
    wherein the right hip-level track screw and the left hip-level track screw are configured to be moved along the left side banner track and the right side banner track to represent an iliac crest level of the patient;
    the poster instrument is further mechanically coupled to upper banner track, which is mechanically coupled to an upper track screw.

2. The instrument of claim 1, wherein the upper banner track, the left side banner track and the right side banner track are immediately adjacent to measurement markings.

3. The instrument of claim 1, wherein the fixed marker and the sliding marker are dry erase markers.

4. The instrument of claim 1, wherein the measuring instrument is mechanically coupled to a horizontal level and a vertical level to increase accuracy.

\* \* \* \* \*